United States Patent
Chen et al.

(10) Patent No.: US 9,192,558 B2
(45) Date of Patent: Nov. 24, 2015

(54) SKIN CARE COMPOSITIONS

(75) Inventors: Minghua Chen, Kobe (JP); Etsuko Yuyama, Kobe (JP); Stanley Pak-Lap Mah, PuDong (CN); Paul Robert Tanner, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1325 days.

(21) Appl. No.: 12/002,165

(22) Filed: Dec. 14, 2007

(65) Prior Publication Data

US 2009/0104129 A1    Apr. 23, 2009

Related U.S. Application Data

(60) Provisional application No. 60/875,146, filed on Dec. 15, 2006.

(51) Int. Cl.
| | |
|---|---|
| *A61K 8/25* | (2006.01) |
| *A61K 47/06* | (2006.01) |
| *A61K 8/49* | (2006.01) |
| *A61Q 19/00* | (2006.01) |
| *A61K 8/81* | (2006.01) |
| *A61K 8/06* | (2006.01) |

(52) U.S. Cl.
CPC ............ *A61K 8/4973* (2013.01); *A61K 8/062* (2013.01); *A61K 8/8147* (2013.01); *A61K 8/8152* (2013.01); *A61Q 19/00* (2013.01); *A61K 2800/33* (2013.01)

(58) Field of Classification Search
None
See application file for complete search history.

(56) References Cited

U.S. PATENT DOCUMENTS

| | | | |
|---|---|---|---|
| 4,781,917 A | 11/1988 | Luebbe et al. | |
| 5,686,082 A | 11/1997 | N'Guyen | |
| 5,686,367 A | 11/1997 | Hayashi | |
| 5,997,887 A | 12/1999 | Ha et al. | |

FOREIGN PATENT DOCUMENTS

WO    WO97/07779    *    3/1997

* cited by examiner

*Primary Examiner* — Tigabu Kassa
(74) *Attorney, Agent, or Firm* — S. Robert Chuey

(57) ABSTRACT

The present invention relates to a skin care composition comprising at least two oil phases dispersed in a continuous aqueous phase comprising a thickening agent, wherein a first oil phase of the oil phases has different composition from the other oil phase, and wherein the composition contains an emulsifier no more than 1.0%. The present invention also relates to a method of preparing a skin care composition comprising dispersing a first oil phase in a continuous aqueous phase comprising a thickening agent; and dispersing a second oil phase in the continuous aqueous phase; wherein composition of said first oil phase differs from composition of said second oil phase, and wherein the composition contains an emulsifier no more than 1.0%.

13 Claims, No Drawings

SKIN CARE COMPOSITIONS

CROSS REFERENCE TO RELATED APPLICATIONS

This application claims the benefit of U.S. Provisional Application No. 60/875,146 filed on Dec. 15, 2006.

FIELD OF THE INVENTION

The present invention relates to skin care compositions, methods of preparing thereof, and methods of use thereof.

BACKGROUND OF THE INVENTION

Many skin care products currently available to consumers are directed primarily to improving the health and/or physical appearance of the skin and/or hair. To provide such benefits, skin care products contains various oily compounds such as emollients and oil-soluble skin actives which usually accompany unpleasant oily or a tacky feel.

Many consumers dislike heavy, oily or greasy feeling compositions and prefer compositions that can provide smooth spreadability and fresh in-use sensory, with smooth silky after-feel. Therefore, while delivery of specific skin actives and compounds that can regulate skin conditions is of course important, consumer acceptance of the sensory aspects such, both prior to and after application, are also important.

Volatile oils such as low viscosity cyclic silicone oils are commonly used in cosmetic compositions for their good cosmetic properties, such as their pleasant feel on contact with the skin due to quick evaporation after they have been applied to skin. However, since skin care compositions contain various non-volatile oils and oil-soluble ingredients, volatility of the volatile oil in final products decreases and the volatile oil does not evaporate quick enough to provide fresh and cool feel on contact with the skin. For example, non-volatile silicones are widely used in skin care products because of their pleasant skin feel qualities as well as their stable oil film formation on the skin which can prevent moisture evaporation from the skin. As the level of non-volatile silicones increases, however, volatility of an oil phase decreases and the product can not provide fresh in-use feeling.

In the meantime, to be most effective, some products must be applied regularly and over an extended period of time. To encourage frequent usage, it is important that the product have a pleasant appearance. For example, a translucent appearance can deliver to consumers pure and light image and still provide rich image.

Based on the foregoing, there is a continuing need to formulate skin care compositions that can provide sensory and aesthetic benefits, especially as related to smooth spreadability and fresh in-use sensory feeling and smooth silky after-feel, optionally being translucent. None of the existing art provides all of the advantages and benefits of the present invention.

SUMMARY OF THE INVENTION

The present invention relates to a skin care composition comprising at least two oil phases dispersed in a continuous aqueous phase comprising a thickening agent, wherein one oil phase of the oil phases has different composition from other oil phase and wherein the composition contains an emulsifier no more than 1.0%.

The present invention also relates to a skin care composition comprising at least two oil phases dispersed in a continuous aqueous phase comprising a thickening agent, wherein one oil phase of the oil phases has different composition from other oil phase and wherein the composition is free from emulsifiers.

The present invention also relates to a method of preparing a skin care composition comprising dispersing a first oil phase in a continuous aqueous phase comprising a thickening agent; and dispersing a second oil phase in the continuous aqueous phase, wherein composition of the first oil phase differs from composition of the second oil phase, and wherein the composition contains an emulsifier no more than 1.0%.

These and other features, aspects, and advantages of the present invention will become evident to those skilled in the art from a reading of the present disclosure.

DETAILED DESCRIPTION OF THE INVENTION

While the specification concludes with the claims particularly pointing and distinctly claiming the invention, it is believed that the present invention will be better understood from the following description.

All percentages and ratios used herein are by weight of the total composition and all measurements made are at 25° C., unless otherwise designated.

As used herein, the "skin care products" are those used to treat or care for, or somehow moisturize, improve, or clean the skin. Products contemplated by the phrase "skin care products" include, but are not limited to moisturizers, personal cleansing products, occlusive drug delivery patches, nail polish, powders, wipes, hair conditioners, skin treatment emulsions, shaving creams and the like.

The term "ambient conditions" as used herein refers to surrounding conditions under about one atmosphere of pressure, at about 50% relative humidity, and at about 25° C. unless otherwise specified.

The compositions of the present invention can include, consist essentially of, or consist of, the components of the present invention as well as other ingredients described herein. As used herein, "consisting essentially of" means that the composition or component may include additional ingredients, but only if the additional ingredients do not materially alter the basic and novel characteristics of the claimed compositions or methods.

All percentages, parts and ratios are based upon the total weight of the skin care compositions of the present invention, unless otherwise specified. All such weights as they pertain to listed ingredients are based on the active level, therefore, do not include carriers or by-products that may be included in commercially available materials, unless otherwise specified.

All publications cited herein are hereby incorporated by reference in their entirety.

The term "keratinous tissue" as used herein, refers to keratin-containing layers disposed as the outermost protective covering of mammals (e.g., humans, dogs, cats, etc.) which includes, but is not limited to, skin, lips, hair, toenails, fingernails, cuticles, hooves, etc.

The term "oil-soluble", as used herein, means when calculating inorganic/organic balance, organic portion is equal or bigger than inorganic portion.

The term "safe and effective amount" as used herein, means an amount of a compound or composition sufficient to significantly induce a positive benefit, preferably a positive keratinous tissue appearance or feel benefit, or positive hair appearance or feel benefit, including independently or in combinations the benefits disclosed herein, but low enough to avoid serious side effects, i.e., to provide a reasonable benefit to risk ratio, within the scope of sound judgment of the skilled artisan.

Herein, "regulating skin condition" means improving skin appearance and/or feel, for example, by providing a benefit, such as a smoother appearance and/or feel. Herein, "improving skin condition" means effecting a visually and/or tactilely perceptible positive change in skin appearance and feel. The benefit may be a chronic benefit and may include one or more of the following: Reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

The term "non-volatile," as used herein, means materials that exhibit a vapor pressure of no more than about 0.2 mm Hg at 25° C. at one atmosphere and/or to materials that have a boiling point at one atmosphere of at least about 300° C. "Volatile," as used herein, all materials that are not "non-volatile" as defined herein.

The term "dispersed" as used herein means a composition where an oil phase is dispersed and suspended in a continuous aqueous phase, including emulsions and non-emulsions.

The composition of the present invention may be used in skin care, cosmetic, and hair care products, non-limiting uses of which include moisturizers, conditioners, anti-aging compounds, skin lightening compounds, and combinations thereof.

The compositions of the present invention provide additional benefits, including stability, absence of significant (consumer-unacceptable) skin irritation and good aesthetics.

The compositions herein may also include a wide variety of other ingredients. The compositions of the present invention are described in detail hereinafter.

Oil Phases

The composition of the present invention comprises at least two oil phases dispersed in a continuous aqueous phase. The composition comprises from about 2% to about 40%, preferably from about 3% to about 25% of oil phases.

The first oil phase has different composition from other oil phases. The first oil phase is preferably a volatile oil phase comprising a volatile oil, preferably at least 80% of a volatile oil by weight of the oil phase. The first oil phase may have a viscosity of from about 0.3 cps to about 100 cps, preferably from about 0.4 cps to about 10 cps, more preferably from about 0.5 cps to about 6 cps. The composition comprises from about 1% to about 30%, preferably from about 2% to about 20% of the first oil phase.

The presence of at least two oil phases can be confirmed using various composition analytical methods including microscopy infrared spectrum technology which can focus on the small oil drop and provide IR spectrum. Each oil phase having different oil composition can be confirmed with a different IR spectrum pattern. Also depending on compositions, dying methods may be used to confirm the presence of at least two oil phases.

The oil phases are understood to be immiscible in an aqueous phase, and may include oil compounds such as natural and synthetic oils and other hydrophobic substances which exhibit limited solubility in an aqueous phase including, but not limited to, oil-soluble ingredients, oil-soluble sunscreens and other oil-soluble skin care actives. Lipids and oils may be derived from animals, plants, or petroleum and may be natural or synthetic.

Suitable oil compounds include both volatile oils and non-volatile oils including, but are not limited to, hydrocarbon oils and waxes, silicone oils, fatty alcohol and fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, salts, isomers and derivatives thereof, and combinations thereof.

Non-limiting examples of non-volatile hydrocarbon oils and waxes suitable for use herein include petrolatum, mineral oil, micro-crystalline waxes, polyalkenes, paraffins, cerasin, ozokerite, polyethylene, perhydrosqualene, poly alpha olefins, hydrogenated polyisobutenes and combinations thereof.

Non-limiting examples of non-volatile silicone oils suitable for use herein include dimethicone copolyol, silicone crosspolymers, dimethylpolysiloxane, diethylpolysiloxane, mixed $C_{1-30}$ alkyl polysiloxanes, phenyl dimethicone, dimethiconol, and combinations thereof. Non-limiting examples of silicone cross-polymers suitable for use herein include acrylate/bis-hydroxypropyl dimethicone crosspolymer, $C_{30-45}$ alkyl cetearyl dimethicone crosspolymer, acrylate/bis-hydroxypropyl dimethicone crosspolymer, $C_{30-45}$ alkyl cetearyl dimethicone crosspolymer, cetearyl dimethicone/vinyl dimethicone crosspolymer, dimethicone crosspolymer, dimethicone crosspolymer-3, dimethicone/phenyl vinyl dimethicone crosspolymer, dimethicone/vinyl dimethicone crosspolymer, diphenyl dimethicone crosspolymer, divinyldimethicone/dimethicone crosspolymer, trifluoropropyl dimethicone/trifluoropropyl divinyldimethicone crosspolymer, vinyl dimethicone/lauryl dimethicone crosspolymer, vinyldimethyl/trimethylsiloxysilicate stearyl dimethicone crosspolymer, polysilicone-11, and mixtures thereof.

Volatile oils useful in the present invention may be selected from the group consisting of volatile silicone oils, volatile hydrocarbons, and mixtures thereof. Volatile oils are disclosed, for example, in Cosmetics, Science, and Technology, Vol. 1, 27-104 edited by Balsam and Sagarin, 1972. Volatile oils useful in the present invention may be either saturated or unsaturated, have an aliphatic character and be straight or branched chained or contain alicyclic or aromatic rings. Examples of preferred volatile hydrocarbons include polydecanes such as isododecane and isodecane (e.g., Permethyl-99A which is available from Presperse Inc.) and the C7-C8 through C12-C15 isoparaffins (e.g., Isopar series available from Exxon Chemicals). Volatile liquid silicone oils are disclosed in U.S. Pat. No. 4,781,917 issued to Luebbe et al. on Nov. 1, 1988, herein incorporated by reference in its entirety. Additionally, a description of various volatile silicones materials is found in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Particularly preferred volatile silicone oils are selected from the group consisting of cyclic volatile silicones corresponding to the formula:

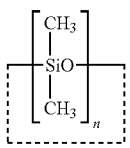

wherein n is from about 3 to about 7; linear volatile silicones corresponding to the formula:

wherein m is from about 1 to about 7; and branched volatile silicones. Highly preferred examples of volatile silicone oils include cyclomethicones of varying viscosities, e.g., Dow Corning 200, Dow Corning 244, Dow Corning 245, Dow Corning 344, and Dow Corning 345, (all from Dow Corning Corp.); SF-1204 and SF-1202 Silicone Fluids (all from G.E. Silicones), GE 7207 and 7158 (all from General Electric Co.); SWS-03314 (all from SWS Silicones Corp.); and KF-995 (from Shin-Etsu Chemical). Preferred examples of liner volatile silicone oils include KF-96A-1cs, KF-96L-1.5cs, KF-96L-2cs, KF-96A-5cs (all from Shin-Etsu Chemical). Preferred examples of branched volatile silicone oils include TMF-1.5 (from Shin-Etsu Chemical).

Aqueous Phase

The composition of the present invention comprises a continuous aqueous phase comprising an aqueous carrier and a thickening agent. The aqueous phase may further comprise other hydrophilic substances which exhibit limited solubility in an oil phase, including but not limited to water-soluble ingredients, water-soluble sunscreens and other water-soluble skin care actives.

The composition comprises from about 60% to about 98%, preferably from about 65% to about 97% of an aqueous phase.

Aqueous Carriers

The aqueous phase of the present invention comprises an aqueous carrier for providing the continuous phase. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol. Preferably, the aqueous carrier is substantially water. Deionized water is preferably used. Water from natural sources including mineral cations can also be used, depending on the desired characteristic of the product.

The pH of the present composition is preferably from about 4 to about 8. When skin benefit agents are included in the aqueous phase, the pH may be adjusted to that which provides optimum efficacy of the active skin benefit agents. Buffers and other pH adjusting agents can be included to achieve the desirable pH. Suitable pH adjusters herein include acetates, phosphates, citrates, sodium hydroxide, triethanolamines, aminomethylpropanol and carbonates.

Thickening Agents

The aqueous phase of the present invention comprises from about 0.1% to about 2%, preferably from about 0.3% to about 1.5% of thickening agents, including thickeners, gelling agents, and structuring agents. The level and species of the thickening agent are selected according to the compatibility with other components, and other desired characteristic of the product.

Nonlimiting classes of thickening agents include crosslinked polyacrylate polymers and copolymers, hydrophobically-modified polyacrylate polymers and copolymers, polyacrylamide polymers and copolymers, polyacryloyldimethyl taurates, aminomethylpropanol (AMP)-based polymers and copolymers, polysaccharides and gums. Useful herein are carboxylic acid/carboxylate copolymers. Non-limiting examples of carboxylic acid/carboxylate copolymers useful herein include: CTFA name Acrylates/C10-30 Alkyl Acrylate Crosspolymer having tradenames Pemulen TR-1, Pemulen TR-2, Carbopol Ultrez 10, Carbopol Ultrez 20, Carbopol Ultrez 21, Carbopol 1342, Carbopol 1382, and Carbopol ETD 2020 (all from Noveon). Commercially available additional water soluble polymers highly useful herein include xanthan gum with tradename KELTROL series available from Kelco; Carbomers with tradenames Carbopol 934, Carbopol 940, Carbopol 950, Carbopol 980 and Carbopol 981 (all from Noveon); acrylates/steareth-20 methacrylate copolymer with tradename ACRYSOL 22 (from Rohm and Hass); polyacrylamide with tradename SEPIGEL 305 (from Seppic); glyceryl polymethacrylate with tradename LUBRAGEL NP, and a mixture of glyceryl polymethacrylate, propylene glycol and PVM/MA copolymer with tradename LUBRAGEL OIL (all from ISP); scleroglucan with tradename Clearogel SC11 (from Michel Mercier Products Inc); ethylene oxide and/or propylene oxide based polymers with tradenames CARBOWAX PEGs, POLYOX WASRs, and UCON FLUIDS (all from Amerchol).

Another class of thickening agents includes a structuring agent. Non-limiting examples of a structuring agents include saturated $C_{12}$ to $C_{30}$ fatty alcohols, saturated $C_{12}$ to $C_{30}$ fatty alcohols containing from about 1 to about 5 moles of ethylene oxide, saturated $C_{12}$ to $C_{30}$ monoglycerol ethers, saturated $C_{12}$ to $C_{30}$ monoglycerol esters, and mixtures thereof, having a melting point of at least about 40° C. A preferred structuring agent of the present invention is selected from the group consisting of stearyl alcohol, cetyl alcohol, behenyl alcohol, Emulsifiers The composition of the present invention may contain an emulsifier, useful for dispersing and suspending the oil phases within the aqueous phase. When the composition of the present invention contains an emulsifier, it contains an emulsifier no more than 1%, preferably no more than 0.5%, and more preferably no more than 0.2%.

A wide variety of emulsifying agents can be employed herein.

In one embodiment, non-limiting examples of which include non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof.

Nonlimiting examples of other emulsifiers for use herein include: polyethylene glycol 20 sorbitan monolaurate (polysorbate 20), steareth-20, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, polyoxyethylene 20 sorbitan trioleate (polysorbate 85), sorbitan monolaurate, polyoxyethylene 4 lauryl ether sodium stearate, polyglyceryl-4 isostearate, hexyl laurate, PPG-2 methyl glucose ether distearate, ceteth-10, diethanolamine cetyl phosphate, glyceryl stearate, PEG 40 hydrogenated castor oil, PEG-60 hydrogenated castor oil, Glycereth-25 PCA Isostearate, and mixtures thereof.

In another embodiment, the emulsifier is a silicone emulsifier, including organically modified organopolysiloxanes (silicone surfactants) such as dimethicone copolyols.

Skin Care Actives

The compositions of the present invention may preferably include at least one skin care active. Without being bound by theory, it is believed the present compositions provide versatility in formulating a variety of actives.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

Vitamin $B_3$ Compounds

Vitamin $B_3$ compound such as niacinamide is a preferred skin care active for use herein. The present invention preferably includes from about 0.1% to about 20%, more preferably from about 0.5% to about 10%, even more preferably from about 2% to about 5% of a vitamin $B_3$ compound.

As used herein, "vitamin $B_3$ compound" means a compound having the formula:

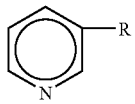

wherein R is —$CONH_2$ (i.e., niacinamide), —$CH_2OH$ (i.e., nicotinyl alcohol); derivatives thereof; and salts of any of the foregoing. Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Whitening Agents

The present compositions may contain a whitening agent. The whitening agent useful herein refers to active ingredients that not only alter the appearance of the skin, but further improve hyperpigmentation as compared to pre-treatment. Useful whitening agents useful herein include ascorbic acid compounds, vitamin $B_3$ compounds, azelaic acid, butyl hydroxy anisole, gallic acid and its derivatives, hydroquinoine, kojic acid, arbutin, mulberry extract, undecylenoyl phenylalanine, and mixtures thereof. Use of combinations of whitening agents is also believed to be advantageous in that they may provide whitening benefit through different mechanisms.

When used, the compositions preferably contain from about 0.01% to about 10%, more preferably from about 0.1% to about 5%, by weight of the composition, of a whitening agent.

Ascorbic acid compounds are useful whitening agents, and have the formula (I):

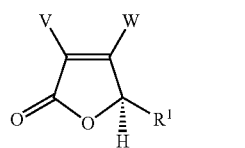

(I)

wherein V and W are independently —OH; R is —CH(OH)—$CH_2OH$; and salts thereof.

Preferably, the ascorbic acid compound useful herein is an ascorbic acid salt or derivative thereof, such as the non-toxic alkali metal, alkaline earth metal and ammonium salts commonly known by those skilled in the art including, but not limited to, the sodium, potassium, lithium, calcium, magnesium, barium, ammonium and protamine salts which are prepared by methods well known in the art.

Flavonoids

The compositions of the present invention may contain a flavonoid compound. Flavonoids are broadly disclosed in U.S. Pat. Nos. 5,686,082 and 5,686,367, both of which are herein incorporated by reference.

Preferred for use herein are substituted flavanones, substituted flavones, substituted chalcones, substituted isoflavones, and mixtures thereof. Some examples of these flavonoids are selected from the group consisting of glucosyl hesperidin, glucosyl rutin, glucosyl myricitrin, glucosyl isoquercitrin, glucosyl quercitrin, methyl hesperidin, and mixtures thereof.

When used, the compositions preferably contain from about 0.01% to about 10%, more preferably from about 0.05% to about 5%, by weight of the composition, of a flavonoid compound.

Peptides

Peptides, including but not limited to, di-, tri-, tetra-, and pentapeptides and derivatives thereof, may be included in the compositions of the present invention in amounts that are safe and effective. As used herein, "peptides" refers to both the naturally occurring peptides and synthesized peptides. Also useful herein are naturally occurring and commercially available compositions that contain peptides.

When included in the present compositions, peptides are preferably included in amounts of from about $1\times10^{-6}$% to about 10%, more preferably from about $1\times10^{-6}$% to about 0.1%, even more preferably from about $1\times10^{-5}$% to about 0.01%, by weight of the composition.

Sugar Amines

The compositions of the present invention may include a safe and effective amount of a sugar amine, which are also known as amino sugars. As used herein, "sugar amine" refers to an amine derivative of a six-carbon sugar. Preferably, the composition contains from about 0.001% to about 20%, more preferably from about 1% to about 10%, even more preferably from about 2% to about 5%, by weight of the composition, of the sugar amine. Examples of sugar amines that are useful herein include glucosamine, N-acetyl glucosamine, mannosamine, N-acetyl mannosamine, galactosamine, N-acetyl galactosamine. Preferred for use herein is glucosamine. Additionally, combinations of two or more sugar amines may be used.

Sunscreen Agents

The compositions of the subject invention may comprise one or more sunscreen actives (or sunscreen agents) and/or ultraviolet light absorbers. Herein, "sunscreen active" includes both sunscreen agents and physical sunblocks. Sunscreen actives and ultraviolet light absorbers may be organic or inorganic. Examples of suitable sunscreen actives and ultraviolet light absorbers are disclosed in The Cosmetic, Toiletry, and Fragrance Association's *The International Cosmetic Ingredient Dictionary and Handbook*, 10th Ed., Gottschalck, T. E. and McEwen, Jr., Eds. (2004), p. 2267 and pp. 2292-93, and further include terephthalylidene dicamphor sulfonic acid (Mexoryl™ SX).

Particulate Materials

The compositions of the present invention may contain a safe and effective amount of a particulate material, preferably a metallic oxide. These particulates can be coated or uncoated, charged or uncharged. Charged particulate materials are disclosed in U.S. Pat. No. 5,997,887, to Ha, et al., incorporated herein by reference. Particulate materials useful herein include iron oxide, mica, mica coated with TiO2, silica, Polymethylsilesquioxane, nylon, polyethylene, talc, styrene, polypropylene, ethylene/acrylic acid copolymer, titanium dioxide, iron oxide, aluminum oxide, silicone resin, calcium carbonate, cellulose acetate, polymethyl methacrylate, and mixtures thereof.

Some examples of a suitable particulate material are ZincOxide, available from BASF as Z-Cote HP1; TiO2, available from Kobo Products Inc. as Kobo GLW75CAP-MP; Polyethylene, available from Equistar Chemicals as Microthene FN 510-00; Polymethylsilesquioxane, available from GE Toshiba as Tospearl 145A, Tospearl 2000 or Tospearl CF600. Preferably, particulate materials are present in the composition in levels of from about 0.01% to about 4%, more preferably from about 0.1% to about 2%, by weight of the composition.

Additional Components

The compositions of the present invention further may comprise humectants, emollients, exfoliants, non-vitamin antioxidants and radical scavengers, hair growth regulators, minerals, preservatives, phytosterols and/or plant hormones, protease inhibitors, tyrosinase inhibitors, anti-inflammatory agents and N-acyl amino acid compounds.

Suitable humectants include, but not limited to, polyhydric alcohols such as polyalkylene glycols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof.

Suitably emollients include, but are not limited to, hydrocarbons, fatty acids, fatty alcohols and esters.

Suitably exfoliants include, but are not limited to, $C_2$-$C_{30}$ alpha-hydroxycarboxylic acids, beta-hydroxycarboxylic acids and salts of these acids.

Suitable non-vitamin antioxidants and radical scavengers include, but are not limited to, BHT (butylated hydroxy toluene), L-ergothioneine (available as THIOTANE™); tetrahydrocurcumin, cetyl pyridinium chloride, carnosine, diethylhexyl syrinylidene malonate (available as OXYNEX™), hexadec-8-ene-1,16-dicarboxylic acid (octadecene dioic acid; ARLATONE™ Dioic DCA from Uniqema), ubiquinone (co-enzyme Q10), tea extracts including green tea extract, yeast extracts or yeast culture fluid (e.g., Saccharomycopsis Ferment Filtrate), and combinations thereof.

Suitable hair growth regulators include, but are not limited to, hexamidine compounds, butylated hydroxytoluene (BHT), hexanediol, panthenol and pantothenic acid derivates, their isomers, salts and derivatives, and mixtures thereof.

Suitable minerals include zinc, manganese, magnesium, copper, iron, selenium and other mineral supplements. "Mineral" is understood to include minerals in various oxidation states, mineral complexes, salts, derivatives, and combinations thereof.

Suitable examples of plant sterols (phytosterols) and/or plant hormones include, but are not limited to, sitosterol, stigmasterol, campesterol, brassicasterol, kinetin, zeatin, and mixtures thereof.

Suitable protease inhibitors include, but are not limited to, hexamidine compounds, vanillin acetate, menthyl anthranilate, soybean trypsin inhibitor, Bowman-Birk inhibitor, and mixtures thereof.

Suitable tyrosinase inhibitors include, but are not limited to, sinablanca (mustard seed extract), tetrahydrocurcumin, cetyl pyridinium chloride, and mixtures thereof.

Suitable anti-inflammatory agents include, but are not limited to, glycyrrhizic acid (also known as glycyrrhizin, glycyrrhixinic acid, and glycyrrhetinic acid glycoside), glycyrrhetenic acid, other licorice extracts, and combinations thereof.

Suitable N-acyl amino acid compounds include, but are not limited to, N-acyl phenylalanine, N-acyl tyrosine, isomers thereof, including their D and L isomers, salts, derivatives, and mixtures thereof. An example of a suitable N-acyl amino acid is N-undecylenoyl-L-phenylalanine commercially available under the tradename SEPIWHITE® from Seppic (France).

Other useful skin care actives include moisturizing and/or conditioning agents, such as Hydrolyzed Viola Tricolor Extract, available from Silab as Aquaphyline; Betaine, available from Degussa as Tego Natural Betaine; glycerol, petrolatum, caffeine, and urea; yeast extracts (e.g., Saccharomycopsis Ferment Filtrate); dehydroepiandrosterone (DHEA), its analogs and derivatives; exfoliating agents, including alpha- and beta-hydroxyacids, alpha-keto acids, glycolic acid and octanoyl salicylate; antimicrobial agents; antidandruff agents such as piroctone olamine, 3,4,4'-trichlorocarbanilide (trichlosan), triclocarban and zinc pyrithione; dimethyl aminoethanol (DMAE); creatine; skin lightening agents such as kojic acid, mulberry extract, hydroquinone, arbutin, and deoxy-arbutin; (sunless) tanning agents, such as dihydroxy acetone (DHA); isomers, salts, and derivatives of any of the foregoing; and mixtures thereof.

Products for Use

In one preferred embodiment, the composition of the present invention contains an emulsifier no more than 1.0%, preferably no more than 0.5%, more preferably no more than 0.2%.

In another preferred embodiment, the composition is free of emulsifiers

In another preferred embodiment, the composition of the present invention has a yield stress in the range of from about 40 Pa to about 1000 Pa, preferably 100 Pa to 500 Pa. A composition having a yield stress lower than 40 Pa may not provide a product stably suspending oil phases over time.

In another preferred embodiment, one of the oil phases in the composition of the present invention is volatile, and preferably comprises a volatile oil selected from the group consisting of volatile silicon oils and volatile hydrocarbon oils.

In another preferred embodiment, the composition of the present invention has translucent appearance, and the Refractive Index (RI) difference between oil phases and aqueous phase is from about 0.001 to about 0.05, preferably from 0.01 to 0.03. Preferably the oil phases have a RI from about 1.38 to about 1.44, more preferably from about 1.39 to about 1.42, and the aqueous phase has a RI from about 1.36 to about 1.42, more preferably from about 1.37 to about 1.39.

The compositions of the present invention may have a viscosity in the range of from about 5,000 cps to about 500,000 cps, preferably from about 10,000 cps to about 200,000 cps.

In these embodiments, the compositions may further comprise at least one compound selected from a group consisting of skin care actives, sun screening agents, humectants, and emollients.

Composition Preparation

The compositions of the present invention are prepared by incorporating at least two oil phases in an aqueous phase, and are generally prepared by conventional methods such as are known in the art of making topical compositions. Such methods typically involve mixing of the ingredients in one or more steps to a relatively uniform state, with or without heating, cooling, application of vacuum, and the like.

In one embodiment, the method of the present invention comprises the steps of:

preparing a low-viscosity oil phase having a viscosity of from about 0.5 cps to about 100 cps, preferably from about 1 cps to about 10 cps;

preparing a second oil phase having different composition from the low-viscosity oil phase;

dispersing the second oil phase in a continuous aqueous phase; and dispersing the low-viscosity oil in the continuous aqueous phase; wherein the composition contains an emulsifier no more than 1.0%.

In another embodiment, the method of the present invention comprises the steps of:

preparing a low-viscosity oil phase having a viscosity of from about 0.5 cps to about 100 cps, preferably from about 1 cps to about 10 cps;

preparing a second oil phase having different composition from the first oil phase;

dispersing the low-viscosity oil phase in a continuous aqueous phase; and dispersing the second oil phase in the continuous aqueous phase; wherein the composition contains an emulsifier no more than 1.0%.

In these embodiments, the low-viscosity oil phase is preferably comprises a volatile oil.

The topical compositions of the present invention may be formulated into a facial skin cosmetic, eye cosmetic, lip cosmetic, scalp hair styling aid, facial hair styling aid, moisturizer, wrinkle soothing serum, lotion, mascara, skin facial mask, skin lotion, skin cream, skin gel, eye gel, eye cream, lip gel, lip cream, cosmetic, foundation, or any other commonly known skin product or treatment.

Test Methods

Yield Stress Measurement

Yield stress can be gained from a curve of shear stress versus shear rate of a composition by extrapolating the curve through the shear stress axis. Here, shear stress is measured by Brookfield DV-II+PRO Digital Viscometer with spindle LV2C or LV3C at 25° C. The spindle rotation speed is set from 0.01 rpm to 5 rpm. At each speed, the shear stress is recorded once the torque reached the maximum. By plotting shear stress versus shear rate, and then fitting with a curve, the yield stress can be obtained at the curve intersect point. When use spindle rotation speed at 0.01 ppm, the shear rate is already very low such as 0.002 (1/S), and the shear stress at this shear rate (0.002/s) can be accepted as the same as the yield stress.

Viscosity Measurement

A viscosity can be measured by a commercially available viscometer like Brookfield DV-II+ PRO Digital Viscometer with shear speed as 5 rpm at 25° C.

Refractive Index Measurement

A refractive Index (RI) can be measured by a commercially available refractometer like Abbe Refractometer (e.g., Atago 3T from Japan) at 25° C.

EXAMPLES

Examples 1-8 represent non-limiting examples of skin care compositions described herein, suitable for application to keratinous tissue in accordance with the methods described herein. The compositions are suitably made as follows.

TABLE 1

| Components (values in wt %) | Ex. 1 | Ex. 2 | Ex. 3 | Ex. 4 |
|---|---|---|---|---|
| A. Oil phase 1 | | | | |
| Cyclopentasiloxane*1 | 4.0 | 4.0 | — | 6.0 |
| Dimethicone-1.5cs*2 | — | — | 5.0 | — |
| Dimethicone-5cs*3 | — | 2.0 | — | — |
| Dimethicone-100cs*4 | — | — | 2.0 | 0.5 |
| Isohexadecane | — | 1.0 | — | — |
| B. Oil phase 2 | | | | |
| Cyclopentasiloxane*1 | — | 4.0 | — | 4.0 |
| Dimethicone-500cs*5 | — | — | 2.0 | — |
| Dimethicone and Dimethiconol*6 | 2.0 | — | 1.0 | — |
| Dow Corning 9040 Silicone Elastomer*7 | — | 4.0 | — | 2.0 |
| Isopropyl Palmitate | — | — | — | 1.0 |
| Laureth-4 | — | — | — | 0.1 |
| Polymethylsilesquioxane*8 | 2.0 | 2.0 | 2.0 | 2.0 |
| C. Aqueous phase | | | | |
| Carbopol 980*9 | — | 0.5 | — | — |
| Carbopol Ultrez 21*10 | 0.5 | — | — | 0.7 |
| Polyacrylamide/C13-14 Isoparaffin/Laureth-7*11 | — | — | 2.0 | — |
| Glycerin | 6.0 | 10.0 | 10.0 | 5.0 |
| Butylene Glycol | 5.0 | — | 5.0 | 10.0 |
| Dipropylene Glycol | 5.0 | — | — | — |
| 1,2-Pentanediol | 3.0 | 3.0 | — | 3.0 |
| 1,2-Hexanediol | — | 1.0 | — | — |
| Symdiol 68*12 | 0.3 | — | 1.0 | — |
| Natural Betaine*13 | 2.0 | 2.0 | — | — |
| Ethanol | 4.0 | — | — | — |
| Niacinamide, USP*14 | 2.0 | — | 3.5 | 5.0 |
| Dexpanthenol, USP | 0.5 | 0.5 | 0.5 | 0.5 |
| Disodium EDTA | 0.025 | 0.025 | 0.025 | 0.025 |
| Lightskin*15 | — | — | — | 1.0 |
| Aquaphyline*16 | 1.0 | — | — | — |
| Glucosyl Hesperidin*17 | — | — | 0.2 | — |
| Promatrixyl*18 | — | 0.4 | — | — |
| Saccharomycopsis Ferment Filtrate*19 | — | — | — | 30.0 |
| Glycereth-25 PCA Isostearate*20 | 0.5 | — | — | — |
| Glydant Plus Liquid*21 | 0.3 | 0.3 | 0.3 | 0.3 |
| Perfume | 0.1 | — | 0.1 | — |
| Sodium hydroxide | adjust pH to 6.0-7.0 | | | |
| Water | qs to 100 | | | |

*1Cyclopentasiloxane: KF-995 available from Shin-Etsu Chemical Co. Ltd.
*2Dimethicone-1.5cs: KF-96L-1.5cs available from Shin-Etsu Chemical Co. Ltd.
*3Dimethicone-5.0cs: KF-96A-5cs available from Shin-Etsu Chemical Co. Ltd.
*4Dimethicone-100cs: KF-96A-100cs available from Shin-Etsu Chemical Co. Ltd.
*5Dimethicone-500cs: KF-96A-500cs available from Shin-Etsu Chemical Co. Ltd.
*6Dimethicone and Dimethiconol: DC Q2-1503 fluid available from Dow Corning Corporation
*7Dow Corning 9040 Silicone Elastomer: available from Dow Corning Corporation
*8Polymethylsilesquioxane: Tospearl CF600 available from GE Toshiba
*9Carbopol 980: available from Noveon
*10Carbopol Ultrez 21: available from Noveon
*11Polyacrylamide/C13-14 Isoparaffin/Laureth-7: Sepigel 305 available from SEPPIC Inc.
*12Symdiol 68: available from Symrise KK
*13Natural Betaine: available from Degussa
*14Niacinamide: available from DSM
*15Lightskin: Agarum Cribosum Extract available from Silab
*16Aquaphyline: Hydroylzed Viola Tricolor Extract available from Silab
*17Glucosyl Hesperidin: Alpha-Ghesperidin PS-CC available from Toyo Sugar Refining
*18Promatrixyl: a mixture contains Palmitoyl Pentapeptide-3 available from Sederma, Inc.
*19Saccharomycopsis Ferment Filtrate: SKII Pitera available from Kashiwayama
*20Glycereth-25 PCA Isostearate: Pyroter GPI-25 available from Ajinomoto
*21Glydant Plus Liquid: available from Lonza Examples 1-4 provide cream type gel compositions and are suitably made as follows:

(1) Phase A: All ingredients are mixed in a vessel using a suitable mixer (e.g., Anchor blade, propeller blade, or IKA T25) until the phase is homogenous.

(2) Phase B: All ingredients are mixed in a vessel using a suitable mixer (e.g., Anchor blade, propeller blade, or IKA T25) until the phase is homogenous. The phase can be heated to about 60° C. or above in order to melt solid oily compounds, if included.

(3) Phase C: Disperse polymer powder or polymer thickener premix in water, and neutralize it to target pH if necessary. Add other water soluble ingredients and mix until the phase is homogenous. Solid ingredients, if any, can be pre-dissolved in part of water and then blend into the aqueous phase.

(4) Slowly add Phase B into Phase C and mix until batch is homogenous. Slowly add Phase A into the mixture of Phase B and Phase C and mix until batch is homogenous. Phase A can be mixed with Phase C prior to mixing Phase B with Phase C.

(5) Add perfume and mix up to homogenously.

TABLE 2

| Components (values in wt %) | Ex. 5 | Ex. 6 | Ex. 7 | Ex. 8 |
|---|---|---|---|---|
| A. Oil phase 1 | | | | |
| Cyclopentasiloxane | 4.0 | 4.0 | — | 6.0 |
| Dimethicone-1.5cs | — | — | 5.0 | — |
| Dimethicone-5cs | — | 2.0 | — | — |
| Dimethicone-100cs | — | — | 2.0 | 0.2 |
| Isohexadecane | — | 1.0 | — | — |
| B. Oil phase 2 | | | | |
| Dimethicone-100cs | — | 3.0 | 2.0 | — |
| Dimethicone and Dimethiconol | 2.0 | — | 1.0 | — |
| Isopropyl Palmitate | 3.0 | — | — | 1.0 |
| Sucrose Polycottonseedate*1 | 0.5 | 0.5 | 0.5 | 0.2 |
| Steareth-21 | — | 0.2 | 0.4 | — |
| Steareth-2 | — | 0.1 | 0.1 | — |
| Cetearyl Glucoside*2 | 0.2 | — | — | 0.2 |
| PEG-100 Stearate*3 | 0.1 | — | — | 0.1 |
| Behenyl Alcohol | 0.4 | 0.4 | 0.4 | 0.4 |
| Stearyl Alcohol | 0.5 | 0.6 | 0.6 | 0.4 |
| Cetyl Alcohol | 0.3 | 0.5 | 0.5 | 0.4 |
| Tocopheryl Acetate | 0.2 | 0.2 | 0.2 | 0.2 |
| Octyl Methoxycinnamate | — | 3.0 | 6.0 | |
| Homosalate | — | — | — | 6.0 |
| Avobenzone | — | — | — | 1.5 |
| Octocrylene | — | — | — | 2.0 |
| Isopropyl Lauroylsarcosinate*4 | — | — | — | 3.0 |
| Zinc Oxide*5 | — | 0.2 | 3.0 | |
| Polymethylsilsesquioxane*6 | 2.0 | 2.0 | — | 2.0 |
| C. Aqueous phase | | | | |
| Water | Qs | qs | qs | qs |
| Carbopol 980 | — | 0.7 | — | — |
| Carbopol Ultrez 21 | 0.7 | — | — | 0.2 |
| Polyacrylamide/C13-14 isoparaffin/laureth-7 | — | — | 2.0 | 2.0 |
| Glycerin | 6.0 | 10.0 | 10.0 | 7.0 |
| Butylene Glycol | 5.0 | 5.0 | 5.0 | |
| 1,2-Pentanediol | — | — | 3.0 | 3.0 |
| D. Active phase | | | | |
| Water | 10 | 10 | 10 | 10 |
| Ethanol | — | — | — | 5.0 |
| KOBO TiO2*7 | 0.8 | — | 1.0 | — |
| Polyethylene Microthene FN 510-00*8 | — | 1.0 | — | 1.0 |
| Niacinamide, USP | 3.5 | 5.0 | 0.5 | 2.0 |
| Dexpanthenol, USP | 0.5 | 0.5 | 0.5 | 0.5 |
| Disodium EDTA | 0.025 | 0.025 | 0.025 | 0.025 |

TABLE 2-continued

| Components (values in wt %) | Ex. 5 | Ex. 6 | Ex. 7 | Ex. 8 |
|---|---|---|---|---|
| Glydant Plus Liquid | 0.5 | 0.5 | 0.5 | 0.5 |
| Perfume | 0.2 | 0.2 | 0.2 | 0.2 |
| Sodium hydroxide | adjust finished product pH to 6.0-7.0 | | | |

*1 Sucrose Polycottonseedate: available from Kobo Products Inc.
*2 Cetearyl Glucoside: Emulgade PL 68/50 available from Cognis
*3 PEG-100 Stearate: Myrj 59P: available from Uniqema
*4 Isopropyl Lauroylsarcosinate: Eldew SL-205 available from Ajinomoto Co.
*5 Zinc Oxide, Z-Cote HP1: available from BASF Corp.
*6 Polymethylsilsesquioxane: Tospearl 145A available from GE Toshiba
*7 KOBO TiO2, Kobo GLW75CAP-MP: available from Kobo Products Inc.
*8 Polyethylene: Microthene FN 510-00: available from Equistar Chemicals Other components: Refer to Table 1

Examples 5-8 provide emulsion compositions and are suitably made as follows (1) Phase A: All ingredients are mixed in a vessel using a suitable mixer (e.g., Anchor blade, propeller blade, or IKA T25) until the phase is homogenous.

(2) Phase B: All ingredients are mixed in a vessel using a suitable mixer (e.g., Anchor blade, propeller blade, or IKA T25) until the phase is homogenous. The phase can be heated to about 70° C. or above in order to melt solid oily compounds, if included.

(3) Phase C: Disperse polymer powder or polymer thickener premix in water, and neutralize it to target pH if necessary. Add other water soluble ingredients. Solid ingredients, if any, can be pre-dissolved in part of water and then be added. Heat to about 70° C. or above and mix until the phase is homogenous.

(4) Phase D: Dissolve all ingredients in partly water. If any insoluble particles but dispersible, disperse them in this phase to make the mixture homogenously.

(5) Slowly add Phase B into Phase C, mix until batch is homogenous, then cool down to about 40° C. or below.

(6) Add Phase D into above mixture of Phase B and Phase C and mix until batch is homogenous.

(7) Add phase A into above mixture of Phase B, Phase C and Phase D and mix until batch is homogenous (8) Add perfume and mix up to homogenously.

According to the Yield Stress Measurement, a shear stress of Example 1 at each spindle rotation speed was measured and yield stress of 176 Pa was obtained. The yield stress of 176 Pa obtained by extrapolation was the same as the data point of shear stress at the lowest shear rate.

| | Spindle rotation speed, (RPM) | | | | | |
|---|---|---|---|---|---|---|
| | 0.01 | 0.05 | 0.1 | 0.5 | 1.0 | 5.0 |
| Shear rate (1/S) | 0.002 | 0.011 | 0.021 | 0.106 | 0.212 | 1.06 |
| Shear stress (Pa) | 176 | 206 | 223 | 279 | 318 | 448 |

It is understood that the foregoing detailed description of examples and embodiments of the present invention are given merely by way of illustration, and that numerous modifications and variations may become apparent to those skilled in the art without departing from the spirit and scope of the invention; and such apparent modifications and variations are to be included in the scope of the appended claims.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition comprising at least two oil phases dispersed in a continuous aqueous phase comprising a thickening agent, wherein a first oil phase has different composition from the other oil phase, and wherein the composition contains an emulsifier no more than 1.0%; wherein said first oil phase comprises a volatile oil and wherein said first oil phase has a viscosity of from about 0.3 cps to about 10 cps.

2. The composition of claim 1, wherein said volatile oils are selected from the group consisting of cyclopentasiloxane, octamethyltrisiloxane, decamethyltetrasiloxane, methyl trimethicone, isododecane and isohexadecane.

3. The composition of claim 1, wherein said first oil phase is volatile.

4. The composition of claim 1, wherein said composition comprises from about 1% to about 30% of said first oil phase.

5. The composition of claim 1, wherein said composition contains an emulsifier no more than 0.5%.

6. The composition of claim 5, wherein said composition contains an emulsifier no more than 0.2%.

7. The composition of claim 1, wherein said composition has a yield stress in the range of from about 40 Pa to about 1000 Pa.

8. The composition of claim 7, wherein said composition has a yield stress in the range of from about 100 Pa to about 500 Pa.

9. The composition of claim 1, wherein said composition further comprises at least one compound selected from the group consisting of skin care actives, sun screening agents, and emollients.

10. The composition of claim 1, wherein the Refractive Index difference between the oil phases and the aqueous phase is from about 0.001 to about 0.05.

11. A skin care composition comprising at least two oil phases dispersed in a continuous aqueous phase comprising a thickening agent, wherein a first oil phase has different composition from the other oil phase, and wherein the composition is free from emulsifiers; wherein said first oil phase comprises a volatile oil and wherein said first oil phase has a viscosity of from about 0.3 cps to about 10 cps.

12. The composition of claim 11, wherein said composition has a yield stress in the range of from about 40 Pa to about 1000 Pa.

13. The composition of claim 12, wherein said composition has a yield stress in the range of from about 100 Pa to about 500 Pa.

* * * * *